United States Patent
Arramon et al.

(10) Patent No.: US 10,206,785 B2
(45) Date of Patent: Feb. 19, 2019

(54) METHODS AND SYSTEMS FOR ENHANCING RADIOGRAPHIC IMAGES OF RADIOLUCENT IMPLANTS

(71) Applicant: Simplify Medical Pty Ltd, Sunnyvale, CA (US)

(72) Inventors: Yves Arramon, Sunnyvale, CA (US); David Hovda, Mountain View, CA (US); Mark Alvis, Santa Cruz, CA (US); Lisa Metelman, Santa Cruz, CA (US)

(73) Assignee: Simplify Medical Pty Ltd (AU)

( * ) Notice: Subject to any disclaimer, the term of this patent is extended or adjusted under 35 U.S.C. 154(b) by 216 days.

(21) Appl. No.: 15/195,874

(22) Filed: Jun. 28, 2016

(65) Prior Publication Data

US 2017/0000623 A1 Jan. 5, 2017

Related U.S. Application Data

(60) Provisional application No. 62/188,551, filed on Jul. 3, 2015.

(51) Int. Cl.
*A61F 2/44* (2006.01)
*A61F 2/30* (2006.01)

(52) U.S. Cl.
CPC .......... *A61F 2/4425* (2013.01); *A61F 2/4455* (2013.01); *A61F 2002/3008* (2013.01); *A61F 2002/30056* (2013.01); *A61F 2002/3082* (2013.01); *A61F 2002/30795* (2013.01); *A61F 2002/30807* (2013.01); *A61F 2002/30827* (2013.01);

(Continued)

(58) Field of Classification Search
CPC .................................................... A61F 2/4425
See application file for complete search history.

(56) References Cited

U.S. PATENT DOCUMENTS 7,585,326 B2  9/2009  De Villiers et al.
8,685,035 B2  4/2014  De Villiers et al.
(Continued)

FOREIGN PATENT DOCUMENTS

WO   WO-2012047279 A1   4/2012

OTHER PUBLICATIONS

International search report and written opinion dated Nov. 22, 2016 for PCT Application No. US-2016040192.

*Primary Examiner* — Andrew Yang

(74) *Attorney, Agent, or Firm* — Wilson Sonsini Goodrich & Rosati

(57) ABSTRACT

A radiolucent intervertebral prosthesis is implanted in an environment that has been prepared in a manner which enhances radiopacity of the prosthesis and/or the environment. A liquid, powder, or other fluid radiopaque (RO) material, such as iohexol, is introduced into an implantation site, either by directly introducing the material into the site and/or by applying the material to a surface of the implant. The presence of the RO material in the implantation site provides contrast with the material of radiolucent prosthesis while the implantation site is being radiographically imaged, e.g. during fluoroscopic visualization while the prosthesis is being implanted. During implantation, the RO material helps the physician view and manipulate the implant, and after the implantation is complete, the RO material will be resorbed or otherwise lost from the implantation site so that the area returns to a radiolucent condition to facilitate subsequent radiographic imaging when needed.

28 Claims, 3 Drawing Sheets

(52) U.S. Cl.
CPC .............. *A61F 2002/30841* (2013.01); *A61F 2002/30904* (2013.01); *A61F 2002/443* (2013.01); *A61F 2002/444* (2013.01)

(56) References Cited

U.S. PATENT DOCUMENTS

| | | |
|---|---|---|
| 8,808,384 B2 | 8/2014 | Arramon |
| 8,845,730 B2 | 9/2014 | De Villiers et al. |
| 9,011,544 B2 | 4/2015 | Arramon et al. |
| 9,351,846 B2 | 5/2016 | De Villiers et al. |
| 2005/0288789 A1 | 12/2005 | Chaouk et al. |
| 2009/0276051 A1 | 11/2009 | Arramon et al. |
| 2010/0312347 A1 | 12/2010 | Arramon et al. |
| 2012/0116515 A1 | 5/2012 | Semler et al. |
| 2013/0110240 A1 | 5/2013 | Hansell et al. |

METHODS AND SYSTEMS FOR ENHANCING RADIOGRAPHIC IMAGES OF RADIOLUCENT IMPLANTS

CROSS-REFERENCE TO RELATED APPLICATIONS

This application claims the benefit of U.S. Provisional No. 62/188,551, filed Jul. 3, 2015, the entire content of which is incorporated herein in its entirety.

BACKGROUND OF THE INVENTION

Field of the Invention

The present invention relates to medical devices and methods. More specifically, the invention relates to methods and systems for enhanced imaging of radiolucent prostheses during implantation.

Back pain takes an enormous toll on the health and productivity of people around the world. According to the American Academy of Orthopedic Surgeons, approximately 80 percent of Americans will experience back pain at some time in their life. In the year 2000, approximately 26 million visits were made to physicians' offices due to back problems in the United States. On any one day, it is estimated that 5% of the working population in America is disabled by back pain.

Common causes of back pain are injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

When a damaged intervertebral disc causes a patient pain and discomfort, surgery is often required. Typically, surgical procedures for treating intervertebral discs involve discectomy (partial or total removal of a disc), often followed by interbody fusion of the superior and inferior vertebrae adjacent to the disc. Fusion is most commonly achieved by implantation of a cage or spacer together with bone graft material to promote bone growth to fuse the adjacent vertebrae together. Oftentimes, pins, rods, screws, cages and/or the like are placed between the vertebrae to act as support structures to hold the vertebrae and bone graft material in place while the bones permanently fuse together.

Of particular interest to the present invention, as an alternative to fusion and pins, approaches have been developed, in which a movable, implantable, artificial intervertebral disc (or "disc prosthesis") is inserted between two vertebrae. A number of different intervertebral disc prostheses are currently being developed. For example, the inventors of the present invention have developed disc prostheses described in U.S. Pat. Nos. 9,351,846; 9,011,544; 8,845,730; and 8,808,384, and others, the full disclosures of which are incorporated by reference. Other examples of intervertebral disc prostheses are the LINK® SB CHARITTE® disc prosthesis (DePuy Spine, Inc.), the MOBIDISK® disc prosthesis (LDR Medical), the BRYAN® cervical disc prosthesis (Medtronic Sofamor Danek, Inc.), the PRODISC® disc prosthesis disc prosthesis (Synthes Stratec, Inc.), and the PCM® disc prosthesis (Cervitech, Inc.).

More recently, the assignee of the present application has proposed to form the endplates of such artificial discs at least partially from polyaryletherketone (PAEK) and other polyaryletherketone (PAEK) polymers which have improved characteristics, including radiolucency (diminished radiopacity) which allows subsequent radiographic imaging to be performed in the area of the implant. See, U.S. Pat. No. 9,011,544 and Patent Publ. Nos. 2010/0312347 and 2009/0276051, the full disclosures of which are incorporated herein by reference. While a significant benefit to the patient, such radiolucency can make initial implantation of the disc more difficult as it can sometimes be challenging to view a radiolucent disc under fluoroscopic imaging which is normally employed during implantation.

Therefore, a need exists for improved radiolucent implants and methods for their implantation under fluoroscopic imaging. In particular, it would be desirable to provide improved methods for implanting radiolucent artificial disc under fluoroscopic imaging as well as improved artificial discs which are modified to be implanted using the improved methods. At least some of these objectives will be met by the inventions described herein below.

Description of the Background Art

U.S. Pat. No. 9,011,544 and Patent Publ. Nos. 2010/0312347 and 2009/0276051 have been described above. Methods for implanting artificial discs of the type described in the present application are described, for example, in U.S. Pat. Nos. 7,585,326 and 8,685,035, the full disclosures of which are incorporated herein by reference.

SUMMARY OF THE INVENTION

According to the present invention, a radiolucent intervertebral prosthesis is implanted in an environment that has been prepared in a manner which enhances radiopacity of the prosthesis and/or implant. A liquid, powder, or other fluid radiopaque (RO) material or contrast agent, such as iohexol, is introduced into an implantation site, either by directly introducing the material into the site and/or by applying the material to a surface of the implant. The presence of the RO material in the implantation site provides contrast with the radiolucent prosthesis while the implantation site is being radiographically imaged, e.g. during fluoroscopic visualization while the prosthesis is being implanted. After the implantation is complete, the RO material will be resorbed or otherwise lost from the implantation site so that the area returns to a radiolucent condition to facilitate subsequent radiographic imaging when desired.

In a first aspect of the present invention, a method for treating a patient having upper and lower vertebrae and an autologous disc in an intervertebral space between the upper and lower vertebrae comprises performing a discectomy to remove the autologous disc from the intervertebral space. An at least partially radiolucent prosthetic disc assembly is configured for implantation into the intervertebral space and has upper and lower ends which are configured to engage the upper and lower vertebrae, respectively, after implantation. The disc assembly will typically be formed from a radiolucent polymer or other material as described below, but may also include components or elements which are not radiolucent, For example, a titanium plasma or other layer may be placed over one or more surfaces of the endplates, so the assembly may have radiopaque features or elements that provide limited image artifacts and not be completely radiolucent.

The radiolucent prosthetic disc is implanted into the intervertebral space in the presence of a fluoroscopic contrast medium (RO material) while fluoroscopically imaging the intervertebral space. Presence of the RO material while positioning the radiolucent prosthetic disc assembly in the intervertebral space provides an enhanced visibility of the boundary between the upper and lower endplates of the radiolucent prosthetic disc assembly and the fluoroscopic contrast medium during such positioning. After the implantation is completed, fluoroscopic contrast medium or other RO material will be lost from the intervertebral space after implantation of the radiolucent prosthetic disc.

The fluoroscopic contrast medium or other RO material may be introduced into the intervertebral space in a variety of ways. In specific embodiments of the present invention, the fluid fluoroscopic contrast medium or other RO material may be coated or otherwise applied over the surface of radiolucent prosthetic disc assembly shortly prior to implantation. Alternatively, the fluid fluoroscopic contrast medium may be pre-coated over the surface of radiolucent prosthetic disc assembly at the time of manufacture. In either case, the fluid over the surface of radiolucent prosthetic disc assembly will be coated or applied in such a way so that the material will be released into the intervertebral space following implantation. Specific examples include dipping, spraying, or painting of the material over the surface(s) of the prosthesis. In still other examples, the fluoroscopic contrast medium or other RO may be injected or otherwise introduced directly into the intervertebral space, before, after, or concurrently with implantation of the prosthesis. Exemplary introductions include injecting or pouring the fluoroscopic contrast medium in liquid, gel, and/or powder form into the intervertebral space. An exemplary liquid fluoroscopic contrast medium comprises iohexol.

In order to provide specific locational information regarding the prosthesis during implantation, collection features may be formed on one or more surfaces of the radiolucent prosthetic disc assembly so that a portion the fluoroscopic contrast medium is preferentially retained in the collection feature during implantation and for a period after the rest of the fluoroscopic contrast medium is lost from the intervertebral space. Exemplary collection features comprise holes, troughs, or capillaries, and the like. Optionally the collection features are arranged in a pattern which is visible during implantation to help discern the orientation of the implant based on the observable orientation of the markers.

In a second aspect of the present invention, a prosthetic disc for insertion between adjacent vertebrae comprises upper and lower endplates having outer surfaces locatable against adjacent vertebrae and inner surfaces. The inner surfaces are configured to allow relative articulation of the plates when the disc is implanted between adjacent vertebral bodies. At least one of said upper and lower endplates is at least partially formed from a radiolucent polymer, and said at least one of said upper and lower plates has one or more collection features formed on a surface thereof, said collection feature being configured to collect and retain fluoroscopic contrast medium to enhance radiographic imaging during implantation.

At least one of said upper and lower endplates of the prosthetic disc is at least partially formed from a radiolucent material, typically a radiolucent polymers having sufficient strength to withstand the stresses encountered in the use. Exemplary radiolucent polymers include polyaryletherketones (PAEK's) with polyetheretherketone (PEEK) being presently preferred.

The collection feature(s) may comprise at least one of a hole, a trough, or a capillary, and the collection feature may be formed on one or more surfaces of the prosthesis, typically, formed on at least an outer surface of one of the endplates, being formed on at least an inner surface of one of the endplates, and/or being formed on at least a peripheral surface of one of the endplates. The collection features may be arranged in patterns that, when observed under fluoroscopic imaging, will provide information regarding the orientation of the prosthesis relative to the patient's anatomy.

The prosthetic disc herein may further comprise a mobile core disposed between inner surfaces of the upper and lower plates, the core arranged to slide and translate with respect to both the upper and lower plates when the prosthetic disc is implanted. The prosthetic disc herein may still further comprise a restraining structure on at least one of the plates configured to hold an outermost periphery of the core captive between the plates during sliding movement of the plates over the core when the prosthetic disc is implanted.

In a third aspect of the present invention, a method for treating a patient comprises preparing an orthopedic implant site for an implant; providing an at least partially radiolucent orthopedic implant configured for implantation into the implant site, the radiolucent orthopedic implant having collection features on a surface thereof; implanting the radiolucent orthopedic implant at the site in the presence of a fluoroscopic contrast medium; allowing the fluoroscopic contrast medium to collect in the collection features on the surface of the implant; and fluoroscopically imaging the intervertebral space while adjusting the position of the radiolucent orthopedic implant, wherein the fluoroscopic contrast medium is visible during such adjusting; wherein the fluoroscopic contrast medium is lost from the intervertebral space after implantation of the radiolucent orthopedic implant.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
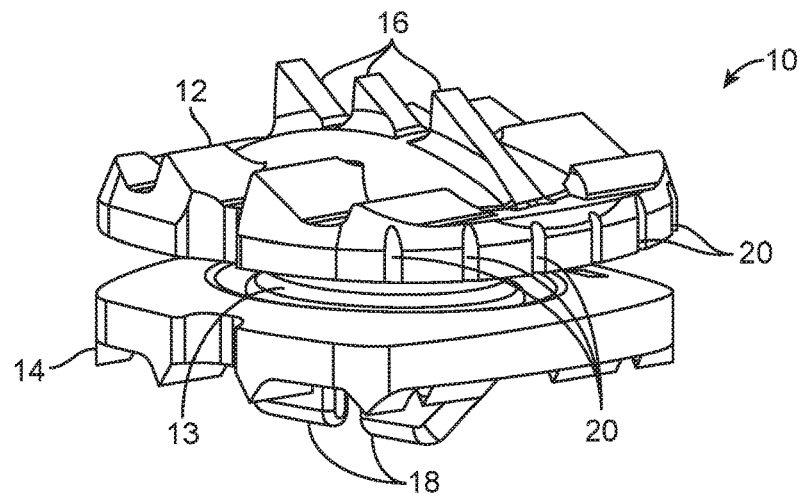
FIG. 1 is in isometric view of an artificial disc having contrast medium collection features formed thereon in accordance with the principles of the present invention.

As shown in FIG. 1, an artificial disc 10 constructed in accordance with the principles of the present invention includes a superior endplate 12 and an inferior endplate 14. The superior endplate and inferior endplate will be configured to articulate relative to each other so that they can act as an active replacement or artificial disc prosthesis when implanted between superior and inferior vertebral bodies in an implantation procedure as described herein below. In the embodiment of FIG. 1, articulation is provided by placing a mobile core 13 having spherical upper and lower surfaces between the endplates 12 and 14, where the core is received in a spherically concave receptacles 15, as shown for example in the lower surface of a superior endplate 12' in FIG. 2. The artificial disc 10 further includes a plurality of superior fins 16 and inferior fins 18 which are provided to stabilize the endplates after implantation, as described in more detail below.

Of particular interest in the present invention, the artificial disc 10 may include a variety of different collection features which are configured to collect and retain fluoroscopic contrast medium in order to enhance radiographic imaging of the artificial disc during implantation. As shown in FIG. 1, six vertical collection features 20 are formed on an anterior lateral surface of the superior endplate 12. During implantation, these collection features 20, which typically comprise shallow channels, troughs, grooves or capillaries, will temporarily collect and retain fluoroscopic contrast medium which is present at the implantation site during the implantation procedure. As the collection features 20 are spaced-apart at fixed distances and oriented vertically relative to the plate, it will be appreciated that viewing the image artifacts produced on the fluoroscopic display will assist the physician in properly positioning the artificial disc 10 as it is being implanted. The contrast medium will however, be absorbed by the surrounding tissue or otherwise lost from the contrast features 22 over time so that the implantation site of the artificial disc 10 will be generally free from radiopaque artifacts after the implantation is complete.

Figure 2:
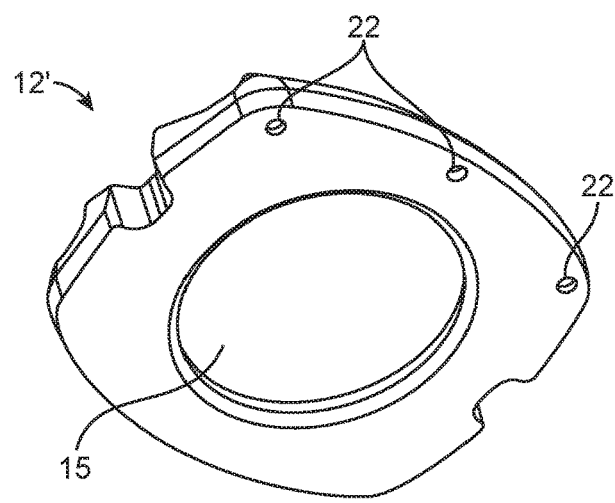
FIG. 2 is a bottom isometric view of a superior endplate of an artificial disc similar to that shown in FIG. 1 except that the contrast medium collection features are formed on a lower surface of the a superior endplate.
Figure 3:
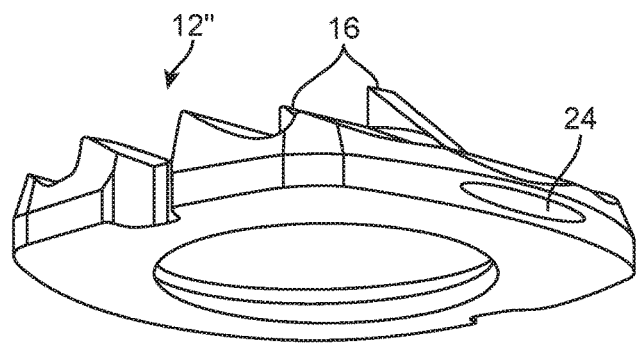
FIG. 3 is an isometric bottom view of a further alternative artificial disc design similar to that of FIG. 1 shown with a superior endplate having a single lateral contrast medium collection feature on an anterior face thereof.

The collection features may be located in a variety of other positions and orientations on the superior endplate, the inferior endplate, and/or the core. As shown in FIG. 2, a series of three small holes, dimples or divots 22 are formed in the lower face of the superior endplate 12'. These collection features 22 will also temporarily collect contrast medium to enhance visibility of the otherwise radiolucent artificial disc during implantation. As shown in FIG. 3, a collection feature 24 is shown as a horizontal or lateral groove, channel or recess in a side surface of the endplate. The horizontal collection feature 24 is formed on the anterior surface of a superior endplate 12".

Although a three piece disc design of a prosthetic disc with a mobile core 13 has been illustrated, the method may also be used with ball and socket and other disc designs. The method is also useful for other spinal implants and orthopedic implants formed of a radiolucent material including poly(aryl-ether-ether-ketone), commonly abbreviated as PEEK, and PEEK composites to improve radiographic imaging of these implants. Implants may include fusion spacers, nucleus replacement devices, fracture fixation devices, joint replacements, such as hips and knees, balls, stems, plates, rods and screws.

Figure 4A:
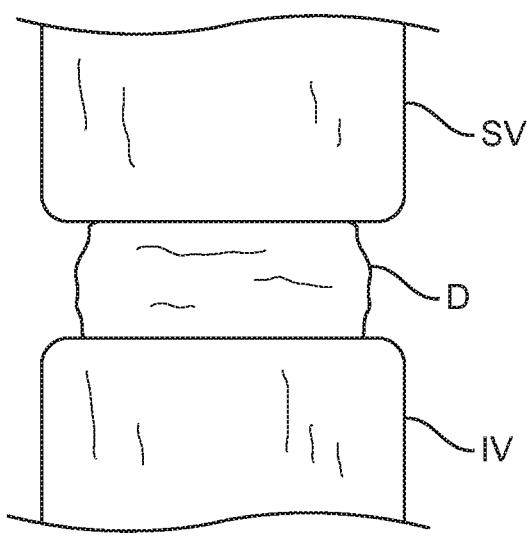
FIGS. 4A through 4D illustrate a method performed in accordance with the principles of the present invention for implanting the artificial disc of FIG. 1 between superior and inferior vertebral bodies.
Figure 4B:
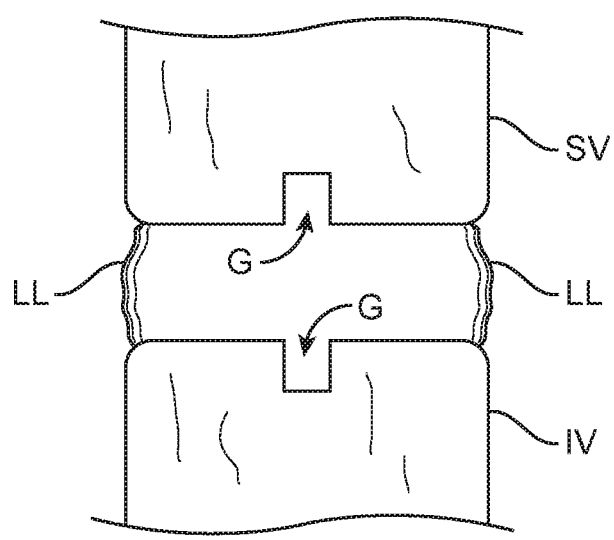
Figure 4C:
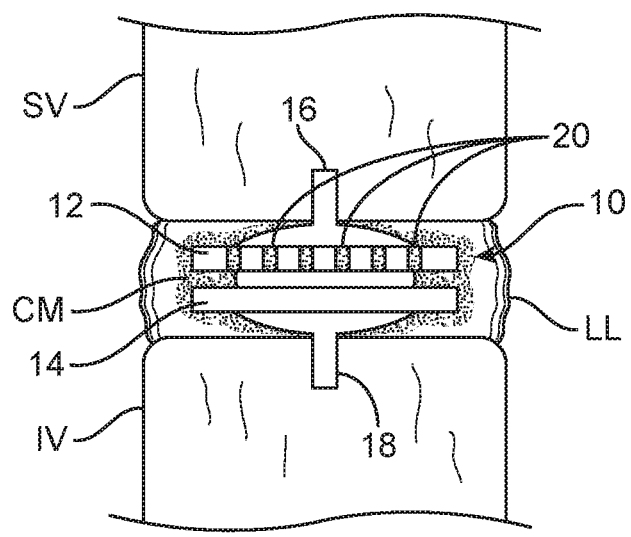

Referring now to FIGS. 4A-4D, a method for implanting the artificial disc 10 is described. Initially, a discectomy is performed to remove the native disc D, as shown in FIG. 4A. After the disc D is removed leaving the lateral ligaments LL in place, a pair of grooves or notches G are formed in the lower face of the superior vertebral body SV and the upper surface of the inferior vertebral body IV, as shown in FIG. 4B. The groves G are sized and shaped to accommodate the fins 16 and 18 and the grooves may be omitted if an implant without fins is to be used. Alternatively, an implant with multiple fins on the superior and inferior endplates would require multiple grooves to be cut in the vertebral bodies. The artificial disc 10 may then be inserted into the space between the superior vertebral body SV and the inferior vertebral body IV as shown in FIG. 4C. Of particular interest to the present invention, a fluoroscopic contrast medium will be present in the implantation site between the superior and inferior vertebral bodies, as shown by a darkened "cloud" around the artificial disc 10 in FIG. 4C. It will be appreciated that the artificial disc 10 itself remains radiolucent, but the disc will occupy a region or volume within the cloud of fluoroscopic contrast medium, thus allowing the peripheral or the outline of the artificial disc to be viewed under fluoroscopic imaging. By providing vertical or other collection features, such as the collection features 20, on the anterior face of the superior endplace 12, the orientation of the disc may be viewed with reference to the accumulation of the contrast medium within these collection features, which accumulations will appear more clearly on the fluoroscopic image.

Figure 4D:
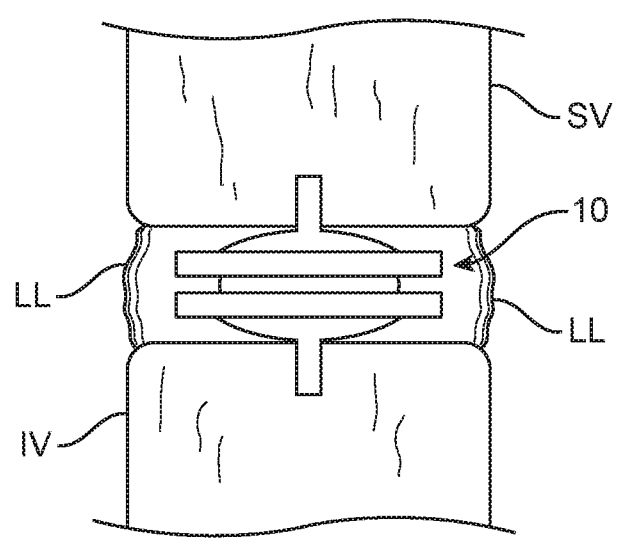

After the implantation is complete, typically over a period of hours or days, the contrast medium (CM) will disappear from the implantation site between the superior vertebral body SV and the inferior vertebral body IV, as shown in FIG. 4D. Once the contrast medium has disappeared, typically by resorption, the region of the spine wherein the artificial disc is implanted may be imaged under various radiographic imaging technologies with minimal interference from the radiolucent disc 10. The time frame for disappearance of the CM may be increased by irrigation or other means. On one example, the contrast medium is no longer visible under fluoroscopy within 1 hour, within 2 hours, within 5 hours, or within 12 hours of insertion of the implant.

Contrast medium can include any of the contrast medium known to be used in the fields of angiography including coronary, pulmonary, interventional, renal or cerebral angiography. Contrast media generally include iodine. They are water soluble, chemically and heat stable, biologically inert and safe. Although for many angiography applications including coronary contrast media would have a low viscosity, such as less than 15 centipoise or less than 10 centipoise at 37 degrees C., contrast media used in this method can have a higher viscosity, such as greater than 10 centipoise or greater than 15 centipoise at 37 degrees C., to remain in the collection features.

The fluoroscopic contrast medium may be injected before, during or after insertion of the radiolucent implant. The injection of the contrast medium may be a one time, multiple time or continuous injection by syringe, catheter, or other injection means.

In an alternative embodiment, the implant may be dipped into the contrast medium before the implant is inserted into the implantation site in the patient. The implant may be coated with the contrast medium in the operating room by one or more of dipping, spraying, or painting. The contrast medium will pool in the collection features and be retained in the collection features by surface tension and/or capillary action. For the dipping method, a higher viscosity contrast medium can be used.

In another alternative embodiment, the implant is coated with the contrast medium or packaged with the liquid contrast medium to provide a combined ready to use implant with contrast.

Examples of contrast agents include iohexol, iopromide, iopromide, and diatrizoate both with and without salt. Agents are available commercially under the brand names Ultravist, Ominipaque, Isovue and Visiopaque. Contrast agents come in different iodine concentrations including high concentrations of 30% iodine or above and low concentrations of less than 30% of iodine. Contrast agent may be in a liquid, gel, and/or powder form.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating a patient, the method comprising:
preparing an orthopedic implant site for an implant;
providing an at least partially radiolucent orthopedic implant configured for implantation into the implant site, the radiolucent orthopedic implant having collection features on a surface thereof;
implanting the radiolucent orthopedic implant at the site in the presence of a fluoroscopic contrast medium;
allowing the fluoroscopic contrast medium to collect in the collection features on the surface of the implant; and
fluoroscopically imaging the intervertebral space while adjusting the position of the radiolucent orthopedic implant, wherein the fluoroscopic contrast medium is visible during such adjusting;
wherein the fluoroscopic contrast medium is lost from the intervertebral space after implantation of the radiolucent orthopedic implant.

2. A method as in claim 1, wherein the orthopedic implant site is in the spine and the orthopedic implant is a spinal implant.

3. A method as in claim 1, wherein the contrast medium has a viscosity greater than 10 centipoise at 37 degrees C.

4. The method of claim 1, wherein the fluoroscopic contrast medium is coated over the radiolucent implant prior to implanting.

5. The method of claim 1, further comprising providing the fluoroscopic contrast medium as a pre-coated assembly prior to implanting.

6. The method of claim 1, wherein the fluoroscopic contrast medium is introduced into the implant site separately from the radiolucent implant.

7. The method of claim 6, wherein the fluoroscopic contrast medium is introduced into the implant site before implantation of the radiolucent implant.

8. The method of claim 6, wherein the fluoroscopic contrast medium is introduced into the implant site after implantation of the radiolucent implant.

9. The method of claim 6, wherein the fluoroscopic contrast medium is introduced into the implant site concurrently with implantation of the radiolucent implant.

10. The method of claim 6, wherein introducing the fluoroscopic contrast medium comprises injecting or pouring the fluoroscopic contrast medium into the implant site.

11. The method of claim 6, wherein the collection features comprise holes, troughs, or capillaries.

12. The method of claim 6, wherein the collection features are arranged in a pattern which is visible during implantation to facilitate observing the orientation of the implant as it is being implanted.

13. A method for treating a patient having upper and lower vertebrae and an autologous disc in an intervertebral space between the upper and lower vertebrae, the method comprising:
performing a discectomy to remove the autologous disc from the intervertebral space;
providing an at least partially radiolucent prosthetic disc assembly configured for implantation into the intervertebral space and having upper and lower ends which are configured to engage the upper and lower vertebrae, respectively, after implantation;
implanting the radiolucent prosthetic disc into the intervertebral space in the presence of a fluoroscopic contrast medium; and
fluoroscopically imaging the intervertebral space while positioning the radiolucent prosthetic disc assembly in the intervertebral space, wherein boundary layers between the upper and lower ends of the radiolucent prosthetic disc assembly and the fluoroscopic contrast medium are visible during such positioning;
wherein the fluoroscopic contrast medium is lost from the intervertebral space after implantation of the radiolucent prosthetic disc.

14. The method of claim 13, wherein the radiolucent implant is formed at least partially from a polyaryletherketone (PAEK).

15. The method of claim 13, wherein the fluoroscopic contrast medium is coated over the radiolucent prosthetic disc assembly prior to implanting.

16. The method of claim 15, further comprising providing the fluoroscopic contrast medium as a pre-coated assembly prior to implanting.

17. The method of claim 16, further comprising coating the fluoroscopic contrast medium over the radiolucent prosthetic disc assembly prior to implanting.

18. The method of claim 15, wherein coating the radiolucent prosthetic disc assembly comprises dipping, spraying, or painting.

19. The method of claim 13, wherein the fluoroscopic contrast medium is introduced into the intervertebral space separately from the radiolucent prosthetic disc.

20. The method of claim 19, wherein the fluoroscopic contrast medium is introduced into the intervertebral space before implantation of the radiolucent prosthetic disc.

21. The method of claim 19, wherein the fluoroscopic contrast medium is introduced into the intervertebral space after implantation of the radiolucent prosthetic disc.

22. The method of claim 19, wherein the fluoroscopic contrast medium is introduced into the intervertebral space concurrently with implantation of the radiolucent prosthetic disc.

23. The method of claim 19, wherein introducing the fluoroscopic contrast medium comprises injecting or pouring the fluoroscopic contrast medium into the intervertebral space.

24. The method of claim 13, wherein the fluoroscopic contrast medium comprises iohexol.

25. The method of claim 13, further comprising collecting portions of the fluoroscopic contrast medium in collection features formed on a surface of the radiolucent prosthetic disc assembly so that a portion the fluoroscopic contrast medium is preferentially retained in the collection features during implantation after the rest of the fluoroscopic contrast medium is lost from the intervertebral space.

26. The method of claim 25, wherein the collection features comprise holes, troughs, or capillaries.

27. The method of claim 25, wherein the collection features are arranged in a pattern which is visible during implantation to facilitate observing the orientation of the prosthesis as it is being implanted.

28. The method of claim 13, wherein the radiolucent prosthetic disc is formed at least partially from a polyaryletherketone (PAEK).

* * * * *